(12) United States Patent
Jho

(10) Patent No.: US 12,374,466 B2
(45) Date of Patent: Jul. 29, 2025

(54) MEDICAL DEVICE INFORMATION TRACKING, ALERT AND INTEGRATION SYSTEM

(71) Applicant: Jiaye Jho, Carlsbad, CA (US)

(72) Inventor: Jiaye Jho, Carlsbad, CA (US)

(*) Notice: Subject to any disclaimer, the term of this patent is extended or adjusted under 35 U.S.C. 154(b) by 463 days.

(21) Appl. No.: 17/220,674

(22) Filed: Apr. 1, 2021

(65) Prior Publication Data

US 2021/0313076 A1 Oct. 7, 2021

Related U.S. Application Data

(60) Provisional application No. 63/005,060, filed on Apr. 3, 2020.

(51) Int. Cl.
| | | |
|---|---|---|
| *G16H 80/00* | (2018.01) | |
| *G16H 20/40* | (2018.01) | |
| *G16H 40/63* | (2018.01) | |
| *G16H 40/67* | (2018.01) | |

(52) U.S. Cl.
CPC ............ *G16H 80/00* (2018.01); *G16H 20/40* (2018.01); *G16H 40/63* (2018.01); *G16H 40/67* (2018.01)

(58) Field of Classification Search
CPC ........ G16H 80/00; G16H 20/40; G16H 40/63; G16H 40/67
See application file for complete search history.

(56) References Cited

U.S. PATENT DOCUMENTS

| | | | | |
|---|---|---|---|---|
| 9,288,614 | B1* | 3/2016 | Young | A61N 1/37254 |
| 9,596,224 | B2* | 3/2017 | Woods | A61N 1/37247 |
| 2003/0028082 | A1* | 2/2003 | Thompson | A61N 1/37282 |
| | | | | 600/300 |
| 2005/0131492 | A1* | 6/2005 | Kroll | G16H 40/63 |
| | | | | 607/60 |
| 2011/0166628 | A1* | 7/2011 | Jain | G16H 40/67 |
| | | | | 709/217 |
| 2014/0328517 | A1* | 11/2014 | Gluncic | G06F 18/00 |
| | | | | 382/103 |
| 2015/0089590 | A1* | 3/2015 | Krishnan | A61N 1/37254 |
| | | | | 607/59 |
| 2016/0270717 | A1* | 9/2016 | Luna | A61B 5/743 |
| 2019/0036886 | A1* | 1/2019 | Wu | H04W 12/61 |
| 2020/0178802 | A1* | 6/2020 | Legay | A61B 5/0031 |
| 2021/0193314 | A1* | 6/2021 | Ghosh | G16H 40/67 |
| 2021/0296008 | A1* | 9/2021 | Novak, Jr. | A61B 5/0022 |
| 2021/0383922 | A1* | 12/2021 | Horton | A61N 1/37252 |
| 2022/0035900 | A1* | 2/2022 | Flakne | A61N 1/37247 |

* cited by examiner

*Primary Examiner* — Maher N Algibhah
(74) *Attorney, Agent, or Firm* — Mintz Levin Cohn Ferris Glovsky and Popeo, P.C.

(57) ABSTRACT

A method of obtaining medical information related to an implanted medical device of a patient comprises detecting that a mobile device is within a predetermined distance of the patient and wirelessly communicating with the implanted medical device or wirelessly obtaining information associated with a Unique Device Identifier of the implanted medical device. Information is displayed on a display of the mobile device.

13 Claims, 3 Drawing Sheets

MEDICAL DEVICE INFORMATION TRACKING, ALERT AND INTEGRATION SYSTEM

CROSS REFERENCE TO RELATED APPLICATIONS

This application claims the benefit of priority under 35 U.S.C. § 119 (e) to U.S. Provisional Patent Application Ser. No. 63/005,060, filed Apr. 3, 2020 and U.S. Provisional Application Ser. No. 62/832,579, filed Apr. 11, 2019. The disclosures of the provisional applications are incorporated by reference in their entireties.

BACKGROUND

Implantable medical devices are devices that are implanted into a patient. Once implanted, the medical device is not typically accessible by a patient. Rather, the device can only be physically accessed by a trained physician, who must surgically or percutaneously access the device through the patient's skin. Further, often times the patient is not part of the decision in the device selection, such as selection of the brand, model, etc. Therefore, after the procedure, the patient does not have the full information on what type of device is implanted and the patient is generally not aware of any information available related to the implanted device.

This can present certain drawbacks. For example, if the patient needs to obtain information about the implanted medical device, such as for example the specifications or brand of the medical device, the patient cannot simply view the medical device due to its implanted state. Even if the patient was previously provided with written records on the implanted medical device, such written records can become misplaced. As a result, it is typically difficult or inconvenient for a patient to easily obtain specifications or other information regarding the particulars of an implanted medical device. In addition to information tracking, often times the manufacturer of a medical device will release new information related to the care and maintenance of the device. Currently there is no easy or obvious way for the new information to reach a patient. This problem not only applies to routine care and maintenance or service-related information but worse yet, also when there's a product recall either initiated by the manufacturer or the regulatory authorities such as the US Food and Drug Agency (FDA), or advisory on the product, the patients cannot be properly informed. This problem is significant especially for patients receiving long term or lifetime implants. However, the same problem can be applicable to medical devices that are only partially, or not implanted as well as short term devices as well.

SUMMARY

In view of the foregoing, there is a need for systems and methods by which a patient, care-taker and/or a clinician can gain access to information related to an implanted medical device and allows the information stored in an accessible way to the patient and/or the care-taker. The systems and methods desirably not require surgical or percutaneous access to the medical device but the device can rather be accessed from an extracorporeal location.

Implementations of the current subject matter may include methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which may include a non-transitory computer-readable or machine-readable storage medium, may include, encode, store, or the like one or more programs that cause one or more processors to perform one or more of the operations described herein. Computer-implemented methods consistent with one or more implementations of the current subject matter may be implemented by one or more data processors residing in a single computing system or multiple computing systems.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

Like reference symbols in the various drawings indicate like elements.

DETAILED DESCRIPTION

Disclosed are systems and methods by which a person can gain access to information related to an implanted medical device. The system includes an application, such as an application residing on a mobile communication device (e.g., a mobile phone, computer, or tablet). The application can wirelessly communicate with a medical device implanted in a person and thereby access a Unique Device Identifier (UDI) of the medical device. The application can then, through an available Application Programming Interface (API), obtain information related to the implanted medical device in relation to the UDI.

The information can include, for example, a device identifier (DI), which is fixed portion of a UDI that identifies the manufacturer, labeler and the specific version or model of a device, and a production identifier (PI), a conditional, variable portion of a UDI that identifies one or more of the following non-limiting examples of information:

a. the lot or batch number within which a device was manufactured;
b. the serial number of a specific device;
c. the expiration date of a specific device;
d. the date a specific device was manufactured;
e. the distinct identification code required by § 1271.290 (c) for a human cell, tissue, or cellular and tissue-based product (HCT/P) regulated as a device;
f. the implanted medical device manufacturer, brand, make, model, and/or specification.

Figure 1:
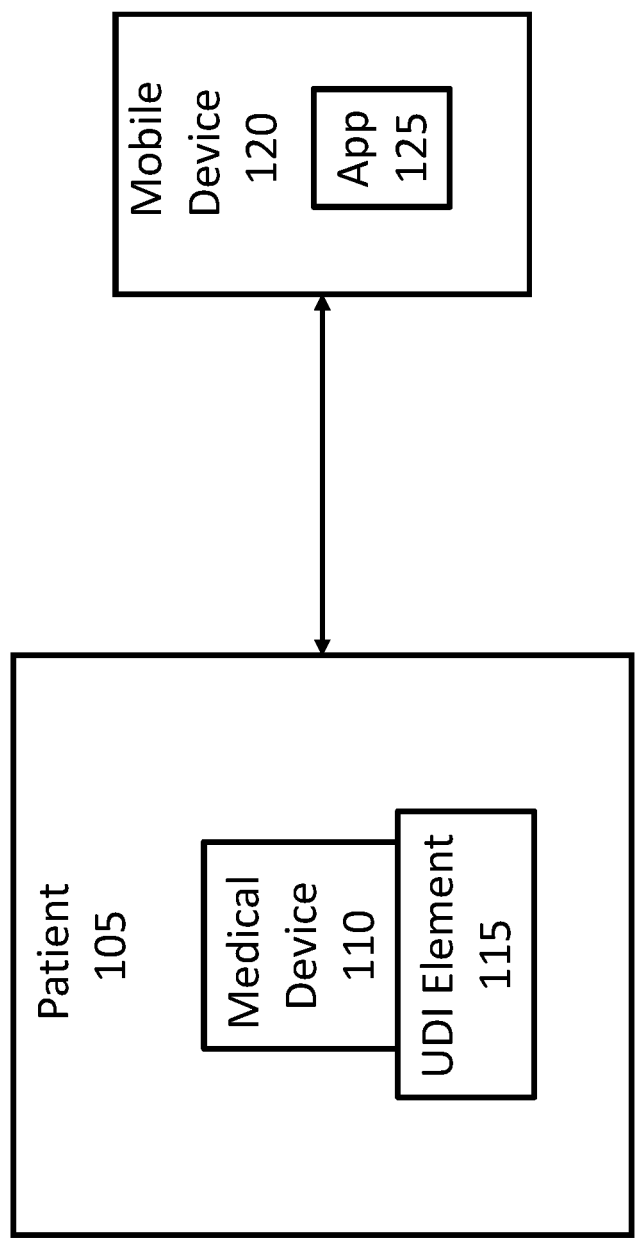
FIG. 1 is a schematic illustration of a medical device system.

FIG. 1 is a block diagram of a medical device identification system illustrating a patient 105 equipped with a medical device 110. In an embodiment, the medical device 110 is implanted within the patient, such as via a surgical procedure or via a percutaneous procedure. The medical device may vary in type and may be, for example, a cardiovascular implant, a spinal implant, orthopedic implant, a joint implant, a spinal plate, a soft tissue reinforcement implant such as a mesh, an infusion device, a soft tissue reinforcement implant a fluid drainage device, any combination or portion thereof, or any other type of implantable medical device. The medical device 110 includes or is otherwise coupled to a Unique Device Identification (UDI) element 115 that identifies the medical device. The UDI element may be on a tag on the medical device itself, or other label such as patient stickers/cards, chart stickers that can be read or otherwise identified wirelessly, such as via a wireless signal or scanning of a code such as bar code or QR code.

With reference still to FIG. 1, the system further includes a mobile device 120 having a mobile application residing thereon. The mobile device can be any type of wireless mobile communication device, such as a mobile phone, smart watch, tablet, computer, or a custom designed dedicated medical product tracking device, etc. The mobile device 120 is configured to wirelessly communicate with the medical device 110 in a manner that enables the mobile device 120 to read or otherwise interpret the UDI element 115. The mobile device can thereby read the UDI element 115 and obtain or download the identifier associated with the UDI element. The application 125 on the mobile device 120 can then store the identifier either in permanent or temporary memory. The type of wireless communication can vary and can include, for example, Bluetooth and Wi-Fi.

The application 125 resides within computer memory of the mobile device 120. The application 125 is configured to provide instructions that are acted upon by the mobile device 120 for causing the mobile device 120 to perform the actions described herein. The application 125 can reside local to the mobile device 120 or it can reside remote to the mobile device 120.

Figure 2:
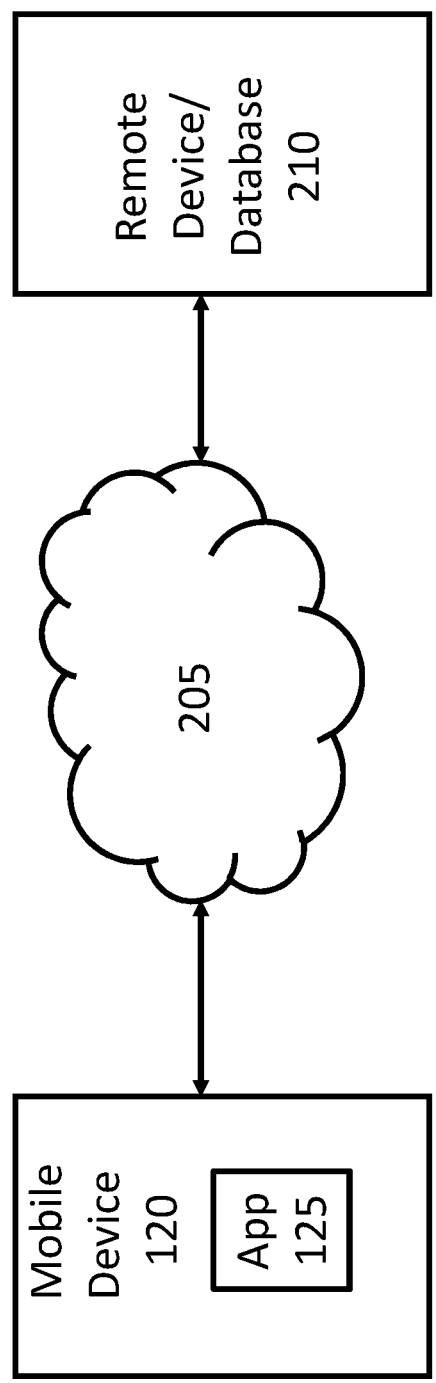
FIG. 2 is a diagram illustrating a healthcare computing environment.

FIG. 2 shows a healthcare computing environment that includes the mobile device 120 and a remote device or database 210. The mobile device 120 can communicate with the remote device/database 210 via a communication network, which can be a telecommunications network 205 that includes or is otherwise coupled to the Internet. The telecommunications network can also include a mobile phone network and/or a local network. The mobile device can communicate the identifier of the UDI element 115 to the remote device/database 210 via the network 205. The remote device/database 210 can then obtain identifying information of the medical device 110 and transfer such identifying information to the mobile device 120 via the network 205.

In another embodiment, the mobile device 120 does not need to communicate with the remote database 210 to obtain the information associated with the UDI. Rather, the mobile device 120 includes a local database that contains information related to UDI's. The mobile device 120 than accesses the local database to obtain the information associated with the UDI.

In a method of use, a user can carry the mobile device 120 on his or her person. The user can be any person and can include a patient, caretaker, clinician, emergency medical responder, police officer, or any other person. The user can then bring the mobile device 120 within a predetermined distance of the patient 105 and thereby within predetermined distance of the medical device 110. The user can then activate the application 120 to cause the application to wirelessly scan the UDI element 115 and obtain the UDI identification data. The application wirelessly communicates with the UDI element during this process. The application can also locally store information related to the UDI element. In an embodiment, the user does not have to activate the application 120 in order for the application to perform the scan. Rather, the application 120 can automatically detect that the mobile device is within a predetermined distance to the UDI element. Once detection has occurred, the application 120 automatically scans the UDI. In embodiments, the mobile device or any aspect of the system is configured to periodically search for recalls, adverse events or alerts related to the implanted medical device; generate an alert or notification to the user of the mobile device and display the information; at the request of the user, search for recalls, adverse events or alerts related to the implanted medical device; generate an alert or notification to the user of the mobile device and display the information; automatically detect that the mobile device is within a predetermined distance of the patient; and/or detect that the mobile device is within a predetermined distance of the patient only after the patient activates an application on the mobile device.

The system is configured to integrate information related to an implanted medical device, wherein such information can include identity, care and maintenance information published by the manufacturer, and adverse events or alert issued by governmental authorities related to the patient's implanted medical device. In an embodiment, the system and/or a software program of the system is configured to enable a patient to interact with other patient(s) with the same or similar implanted medical device identified by the Unique Device Identifier. The patient can use the mobile app to interact with the medical device manufacturer such to submit questions and/or submit user complaints to the medical device manufacturer through the information obtained with the Unique Device Identifier.

The application can then transmit the UDI identification data to the remote device/database 210 via the network 205. The remote device/database 210 via the network 205 can then transmit identifying data to the application 125 via the network 205.

In another embodiment, the application and/or the mobile device includes a local database that includes information related to UDI information. The mobile device does then not need to communicate with the database 210 via the network 205. Rather, the application simply accesses the local database to obtain the relevant information. The application can periodically communicate with the remote database 210 to update the locally-stored information.

The mobile device can also include a display 120 that renders a graphical user interface that characterizes various aspects regarding the operation of the medical device 110. In some implementations, the graphical user interface displayed in the display includes a plurality of graphical user interface elements which, when activated via user-generated input, causes either a mode of operation of the medical device or the mobile device 120 to change and/or a view presented in the graphical user interface of the display to change. The user-generated input can be via various modalities including, for example, the display if it includes a capacitive or other touch screen interface, mechanical buttons/knobs/sliders external to the display 115, and the like.

In other variations, the application 125 can download or access software that can affect a mode of operation or update software/firmware that is executed by the medical device 110.

Various devices and systems, both local to the mobile device 120 and remote to the mobile device 120, can interact via the network 205 (which can be one of a plurality of networks). The computing network 205 can provide any form or medium of digital communication connectivity (i.e., wired or wireless) amongst the various devices and systems. Examples of communication networks include a local area network ("LAN"), a wide area network ("WAN"), WIFI, and the Internet. In some cases, one or more of the various devices and systems can interact directly via peer-to-peer coupling (either via a hardwired connection or via a wireless protocol such as BLUETOOTH, ZIGBEE, short range radio, Wi-Fi, etc.). In addition, in some variations, one or more of the devices and systems communicate via a cellular or satellite data network.

The medical device 110 and mobile device 120 can each include at least one communications interface that can access the computing network 205 either via a fixed wired connection or via a wireless connection (via, for example, one or more access points). The mobile device 120 can transmit data via the computing network 205 to any of the other components within a computing landscape that can, for example, characterize the medical device 110. In addition, the medical device 110 can receive data from the computing network 205 relating to monitoring and in some cases controlling one or more attributes of the medical device 110 (e.g., software updates, configuration updates, historical data, status information, assets location, patient information, etc.).

In particular, aspects of the computing landscape 200 can be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. A client and server are generally remote from each other and typically interact through the communications network 205. The relationship of the clients and servers arises by virtue of computer programs running on the respective computers and having a client-server relationship to each other. Clients can be any of a variety of computing platforms that include local applications for providing various functionality within the healthcare environment. Example clients include, but are not limited to, desktop computers, laptop computers, tablets, and other computers with touch-screen interfaces. The local applications can be self-contained in that they do not require network connectivity and/or they can interact with one or more of the servers (e.g., a web browser).

The UDI information stored on the mobile device, or middleware or data server associated with the user or his/her device, allows new information about the medical device such as complaints, service advisories from the manufacturer, recalls from either the manufacturer or regulatory agencies such as the FDA to be transmitted too the user in the form of notifications.

A variety of applications can be executed on the various devices and systems within the computing landscape including the medical devices such as electronic health record applications, medical device monitoring, operation, and maintenance applications, scheduling applications, alert applications, billing applications and the like. As a further example, the applications can provide for remote alarms management and/or asset tracking for the medical devices 110.

The network 130 can be coupled to one or more data storage systems. The data storage systems can include databases providing physical data storage within the healthcare environment or within a dedicated facility. In addition, or in the alternative, the data storage systems can include cloud-based systems providing remote storage of data in, for example, a multi-tenant computing environment. The data storage systems can also comprise non-transitory computer readable media.

Various types of communication protocols can be used by the mobile device 120 including, for example, messaging protocols such as SMS and MMS. In some cases, the mobile device 120 can receive alerts generated from the operation of the medical devices 110 and/or they can otherwise be used to monitor the operation of such medical devices 110.

Figure 3:
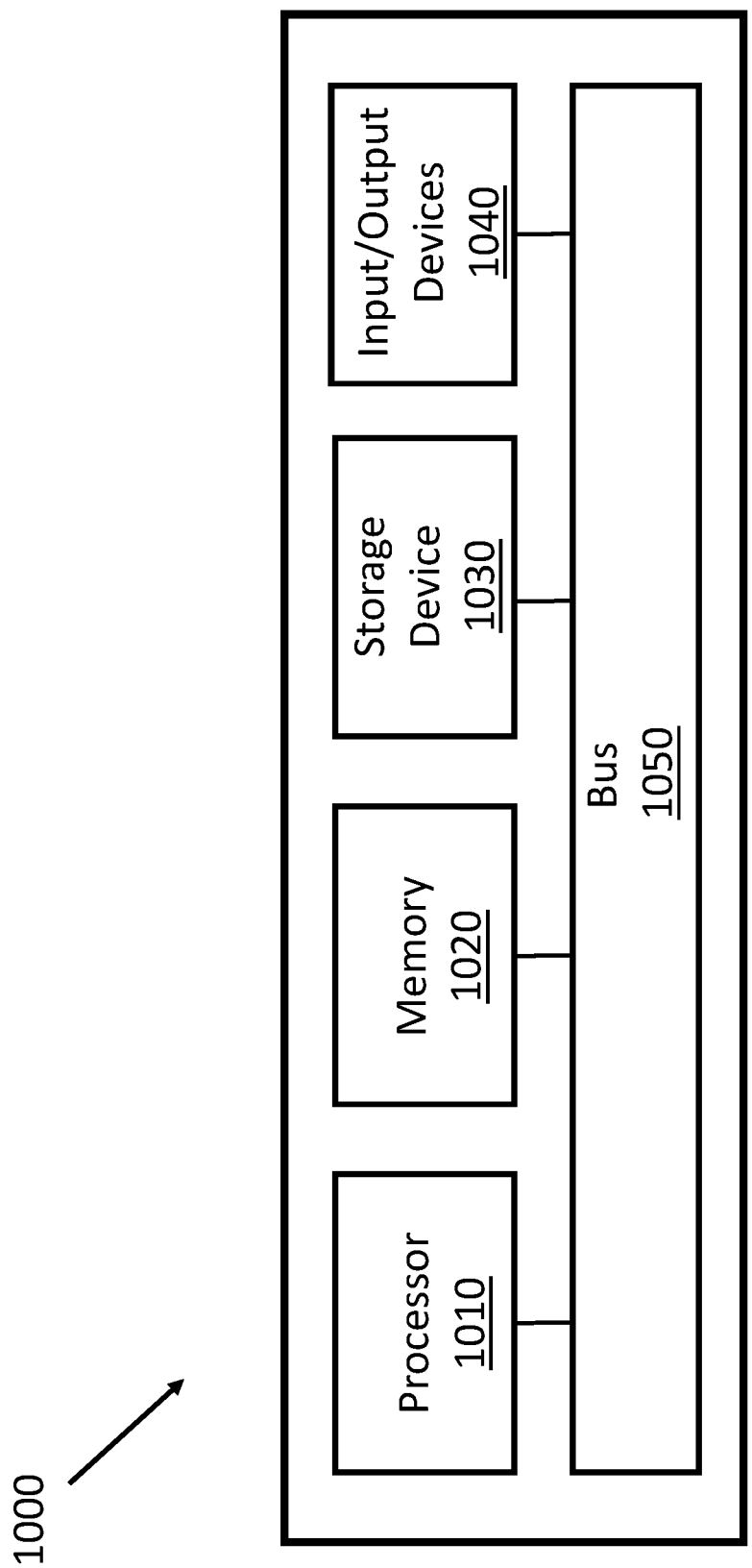
FIG. 3 depicts a block diagram illustrating a computing system 1200 consistent with implementations of the current subject matter.

FIG. 3 depicts a block diagram illustrating a computing system 1200 consistent with implementations of the current subject matter. For example, the computing system 1000 may implement a user equipment, a personal computer, or a mobile device.

As shown in FIG. 3, the computing system 1000 may include a processor 1010, a memory 1020, a storage device 1030, and an input/output device 1040. The processor 1010, the memory 1020, the storage device 1030, and the input/output device 1040 may be interconnected via a system bus 1050. The processor 1010 is capable of processing instructions for execution within the computing system 1000. Such executed instructions may implement one or more components of, for example, cross-cloud code detection. In some example embodiments, the processor 1010 may be a single-threaded processor. Alternately, the processor 1010 may be a multi-threaded processor. The processor 1010 is capable of processing instructions stored in the memory 1020 and/or on the storage device 1030 to display graphical information for a user interface provided via the input/output device 1040.

The memory 1020 is a non-transitory computer-readable medium that stores information within the computing system 1000. The memory 1020 may store data structures representing configuration object databases, for example. The storage device 1030 is capable of providing persistent storage for the computing system 1000. The storage device 1030 may be a floppy disk device, a hard disk device, an optical disk device, or a tape device, or other suitable persistent storage means. The input/output device 1040 provides input/output operations for the computing system 1000. In some example embodiments, the input/output device 1040 includes a keyboard and/or pointing device. In various implementations, the input/output device 1040 includes a display unit for displaying graphical user interfaces.

According to some example embodiments, the input/output device 1040 may provide input/output operations for a network device. For example, the input/output device 1040 may include Ethernet ports or other networking ports to communicate with one or more wired and/or wireless networks (e.g., a local area network (LAN), a wide area network (WAN), the Internet, a public land mobile network (PLMN), and/or the like).

In some example embodiments, the computing system 1000 may be used to execute various interactive computer software applications that may be used for organization, analysis and/or storage of data in various formats. Alternatively, the computing system 1000 may be used to execute any type of software applications. These applications may be used to perform various functionalities, e.g., planning functionalities (e.g., generating, managing, editing of spreadsheet documents, word processing documents, and/or any other objects, etc.), computing functionalities, communications functionalities, etc. The applications may include various add-in functionalities or may be standalone computing items and/or functionalities. Upon activation within the applications, the functionalities may be used to generate the user interface provided via the input/output device 1040.

The user interface may be generated and presented to a user by the computing system 1000 (e.g., on a computer screen monitor, etc.).

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random-access memory associated with one or more physical processor cores.

With certain aspects, to provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive track-pads, voice recognition hardware and software, optical scanners, optical pointers, digital image capture devices and associated interpretation software, and the like.

The computing system may include clients and servers. A client and server are generally remote from each other and typically interact through a communication network. The relationship of client and server arises by virtue of computer programs running on the respective computers and having a client-server relationship to each other.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) depicted in the accompanying figures and/or described herein do not necessarily require the particular order shown, or sequential order, to achieve desirable results. Other implementations may be within the scope of the following claims.

What is claimed is:

1. A method of obtaining medical information related to an implanted medical device of a patient, comprising:

detecting that a mobile device is within a predetermined distance of the patient, wherein the mobile device is a smart watch being worn by the patient;

wirelessly communicating, by the mobile device and while the mobile device is being worn by user, with the implanted medical device or wirelessly obtaining information associated with a Unique Device Identifier of the implanted medical device, wherein the mobile device periodically searches solely in a local database of the mobile device for recalls related to the implanted medical device based on the Unique Device Identifier of the implanted medical device, and wherein the mobile device searches solely in a local database of the mobile device for an alert issued by governmental authorities related to the patient's implanted medical device, and wherein the searches are conducted without interaction with a device other than the mobile device and the implanted medical device, and wherein the mobile device interacts with a second patient having a similar implanted medical device base on the Unique Device Identifier of the Implanted Medical Device; and displaying information regarding a recall of the implanted medical device on a display of the mobile device.

2. The method of claim 1, wherein the information is obtained from local database of the mobile device.

3. The method of claim 1, wherein the information includes the implanted medical device manufacturer, brand, make, model, specification, a lot or batch number within which the implanted medical device was manufactured, a serial number of the implanted medical device, an expiration date of the implanted medical device, or a date the implanted medical device was manufactured.

4. The method of claim 1, wherein the implanted medical device is a prosthetic implant, a cardiovascular implant, a spinal implant, an orthopedic implant, a joint implant, a soft tissue reinforcement implant, an aesthetic implant, an infusion device, or a fluid drainage device.

5. The method of claim 1, further comprising periodically updating a local database with the information associated with the Unique Device Identifier of the implanted medical device.

6. The method of claim 1, wherein additional information related to the implanted medical device can be stored on the mobile device for ease of patient access.

7. The method of claim 1, wherein the mobile device generates an alert or notification related to a recall of the implanted medical device to the user of the mobile device and display the information.

8. The method of claim 1, wherein the mobile device at the request of the user, searches for recalls, adverse events or alerts related to the implanted medical device.

9. The method of claim 8, wherein the mobile device generates an alert or notification to the user of the mobile device and display the information.

10. The method of claim 1, wherein the mobile device automatically detects that the mobile device is within a predetermined distance of the patient.

11. The method of claim 1, wherein the mobile device detects that the mobile device is within a predetermined distance of the patient only after the patient activates an application on the mobile device.

12. The method of claim 1, wherein wirelessly obtaining information associated with a Unique Device Identifier of the implanted medical device comprises querying a remote database via a telecommunication network regarding a recall of the medical device based on the Unique Device Identifier of the implanted medical device.

13. The method of claim 1, further comprising automatically submitting a question to a manufacturer of the implanted medical device regarding a recall.

\* \* \* \* \*